(12) United States Patent
Lipshaw

(10) Patent No.: US 7,867,185 B2
(45) Date of Patent: Jan. 11, 2011

(54) GRADUATED COMPRESSION DEVICE FOR THE TREATMENT OF CIRCULATORY DISORDERS

(75) Inventor: Moses A. Lipshaw, Encinitas, CA (US)

(73) Assignee: CircAid Medical Products, San Diego, CA (US)

( * ) Notice: Subject to any disclaimer, the term of this patent is extended or adjusted under 35 U.S.C. 154(b) by 133 days.

(21) Appl. No.: 12/166,188

(22) Filed: Jul. 1, 2008

(65) Prior Publication Data
US 2010/0004563 A1 Jan. 7, 2010

(51) Int. Cl.
*A61L 15/00* (2006.01)
(52) U.S. Cl. .............................. 602/75; 602/60; 602/61; 602/62
(58) Field of Classification Search ................. 602/5, 602/13, 20–23, 26–27, 60–62, 75; 128/882
See application file for complete search history.

(56) References Cited

U.S. PATENT DOCUMENTS

| 5,533,963 A * | 7/1996 | Hall | 602/75 |
| 6,846,295 B1 * | 1/2005 | Ben-Nun | 601/152 |
| 2007/0179420 A1 * | 8/2007 | Daneshvar | 602/75 |

* cited by examiner

*Primary Examiner*—Michael A. Brown
(74) *Attorney, Agent, or Firm*—Gordon & Rees LLP

(57) ABSTRACT

A method of applying therapeutic compression to a patient's body limb, by: (a) measuring the dimensions of a patient's body limb; (b) determining a desired compression profile for the patient's body limb; and (c) forming a compression device comprising a plurality of tension bands dimensioned to be wrapped around the patient's limb, wherein different tension bands have different widths such that applying an equal tension to the bands results in different compressions being applied along the length of the patient's limb such that the desired compression profile is applied to the patient's limb.

12 Claims, 5 Drawing Sheets

GRADUATED COMPRESSION DEVICE FOR THE TREATMENT OF CIRCULATORY DISORDERS

TECHNICAL FIELD

The present invention is related to devices that apply compression to body limbs for the treatment of edema, lymphedema and various venous disorders.

BACKGROUND OF THE INVENTION

Many compression systems currently exist for treating edema, lymphedema and various venous disorders by exerting pressure inwardly on a patient's body limb. However, several common problems with these systems have emerged. First, each patient's body shape is unique and most systems do not allow for optimal fitting to each and every uniquely shaped body limb. Second, the locations and levels of where therapeutic compression is best applied to a patient's limb are unique for each patient. Unfortunately, existing systems for applying the prescribed pressure profile to the limb typically involve inserting foam layers under regions of a compression garment to alter limb circumference, pulling different bands (of a multi-band compression garment) of the same width to different tensions, or manufacturing a multi-band compression garment or a tubular elastic compression stocking with the material's stretch characteristics varying along the length of the garment in an effort to create different tensions. The disadvantages of these approaches are that they are complex, requiring skill, time and materials and often the resulting compression profile may even be ignored. Third, many existing systems have the disadvantage of being hard to put on and are limited to elastic compression materials. If elastic stockings were made non-elastic and did not stretch (thereby not allowing a large circumference of a body part to pass through an area dimensioned to fit a smaller circumference of the body part), they would be impossible to don. The values of elastic compression versus non-elastic compression also differ in resting compression created by elasticity.

It would instead be ideal to provide a solution that is customized to each patient's unique body shape and medical needs, and also be easy to put on and use.

SUMMARY OF THE INVENTION

In one aspect, the present invention provides a method of applying therapeutic compression to a patient's body limb, comprising: (a) measuring the dimensions of a patient's body limb; (b) determining a desired compression profile for the patient's body limb; and (c) forming a compression device comprising a plurality of tension bands dimensioned to be wrapped around the patient's limb, wherein different tension bands have different widths such that applying an equal tension to the bands results in different compressions being applied along the length of the patient's limb such that the desired compression profile is applied to the patient's limb.

First, the dimensions of a patient's body limb (e.g.: its length and circumferences) are determined at different lengths along the body limb. Next, a desired compression profile is determined for the particular patient being assessed. Finally, the compression device is manufactured (to be unique to the patient) such that tension bands with different widths apply different compressions along the length of the device, thus applying the desired compression profile to the limb.

In various aspects, the compression forces may increase, decrease or vary along the length of the limb. The particular compression force profile will depend upon the particular needs of the patient for which it is designed.

The present invention also optionally comprises: (a) wrapping the tension bands of the compression device around the patient's limb; and (b) applying equal tension to the bands, such that the different bands apply different pressures along the length of the limb, thereby applying the desired compression profile to the patient's limb.

The present invention also comprises a compression garment for applying therapeutic compression to a patient's body limb, comprising: an elongated body dimensioned to be wrapped around a length of a patient's limb to apply a therapeutic compression to the limb; and a plurality of tension bands along the length of the elongated body, the tension bands being of different widths such that applying an equal tension to the bands results in different compressions being applied by the bands along the length of the patient's limb, and wherein the elongated body and the tension bands are manufactured based upon measurements of a particular patient's body limb and a desired compression profile for the particular patient's body limb such that a desired compression profile is applied to the patient's limb when the tension bands are wrapped around the patient's limb. The tension bands themselves may be elastic, non-elastic, or have any stretch characteristic in between.

An advantage of the present invention is that the compression device it uniquely tailored to the particular patient (or group of similar patients) for which it is designed.

A second advantage of the present invention is that its unique compression profile (i.e.: different compressions being applied at different points along the length of the limb) can be generated by applying the same tensions to the various tension bands along the length of the device. This makes application of the device fast and easy. Moreover, the inclusion of a "tension gage" to separately measure (and then apply) different tensions in each of the bands can increase the accuracy of the compression profile.

BRIEF DESCRIPTION OF THE DRAWINGS AND TABLES

Figure 3:
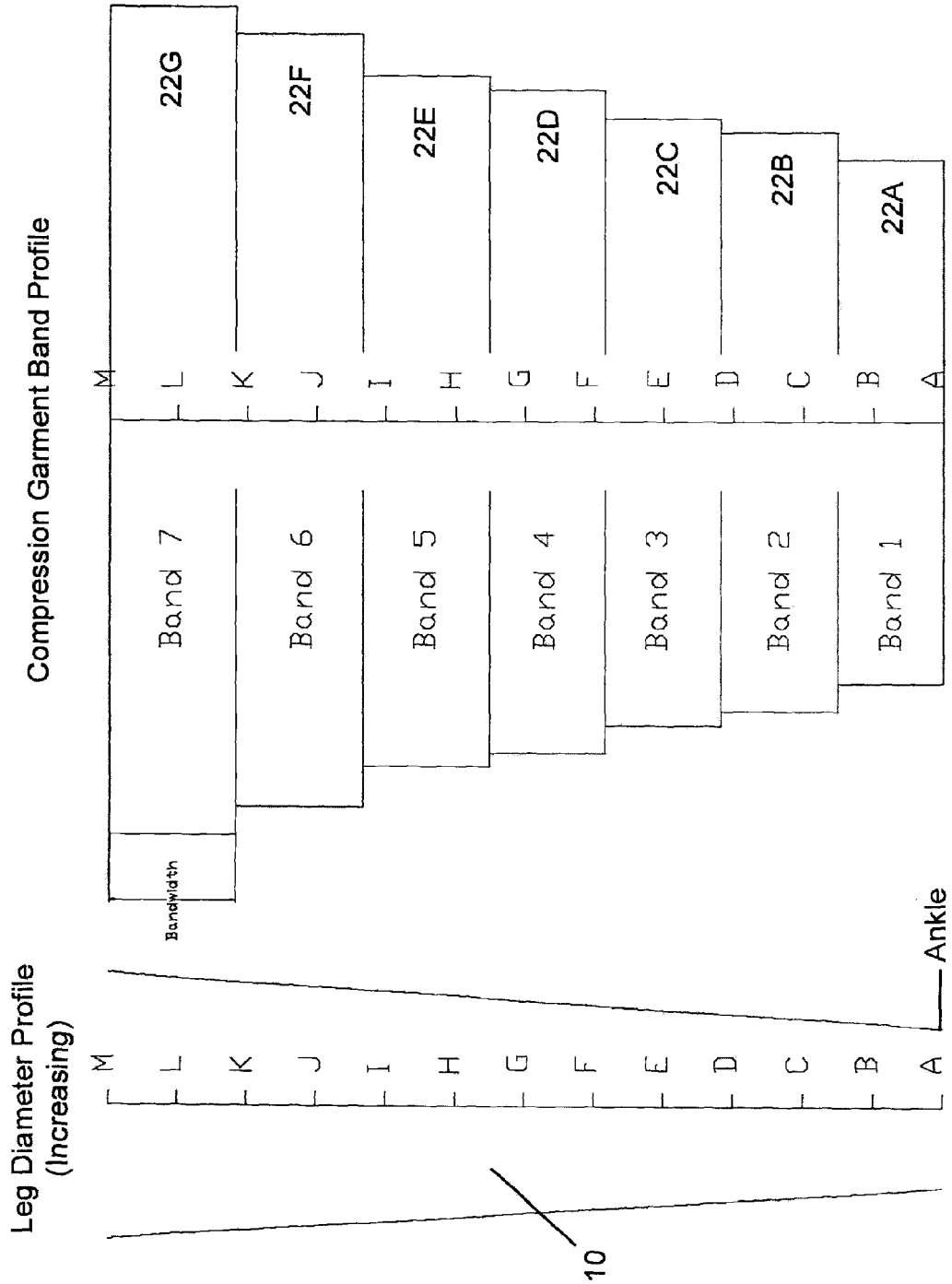
FIG. 3 is an illustration of a increasing leg circumference profile, and a compression garment designed to achieve the desired compression profile. The desired compression profile is 30-40 mmHg of compression at the ankle with a compression profile that progressively decreases along the length of the leg (from location A to M—i.e.: from the groin to the ankle).

Table 1A is a leg dimension profile corresponding to FIG. 3.

Table 1B is a compression garment dimension and compression profile corresponding to FIG. 3.

Figure 4:
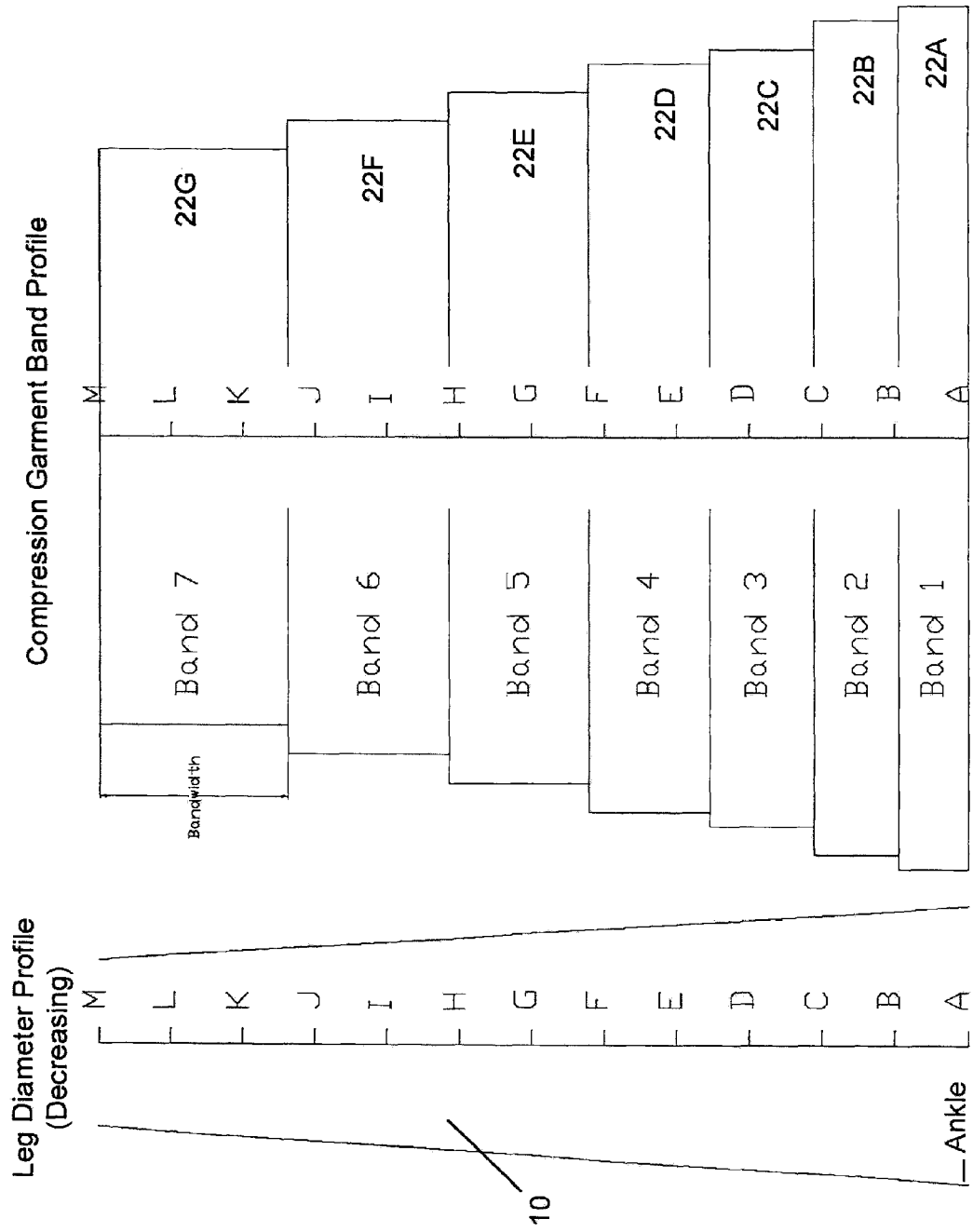

FIG. 4 is an illustration of a decreasing leg circumference profile, and a compression garment designed to achieve the desired compression profile. The desired compression profile is 30-40 mmHg of compression at the ankle with a compression profile that progressively decreases along the length of the leg (from location A to M—i.e.: from the groin to the ankle).

Table 2A is a leg dimension profile corresponding to FIG. 4.

Table 2B is a compression garment dimension and compression profile corresponding to FIG. 4.

Figure 5:
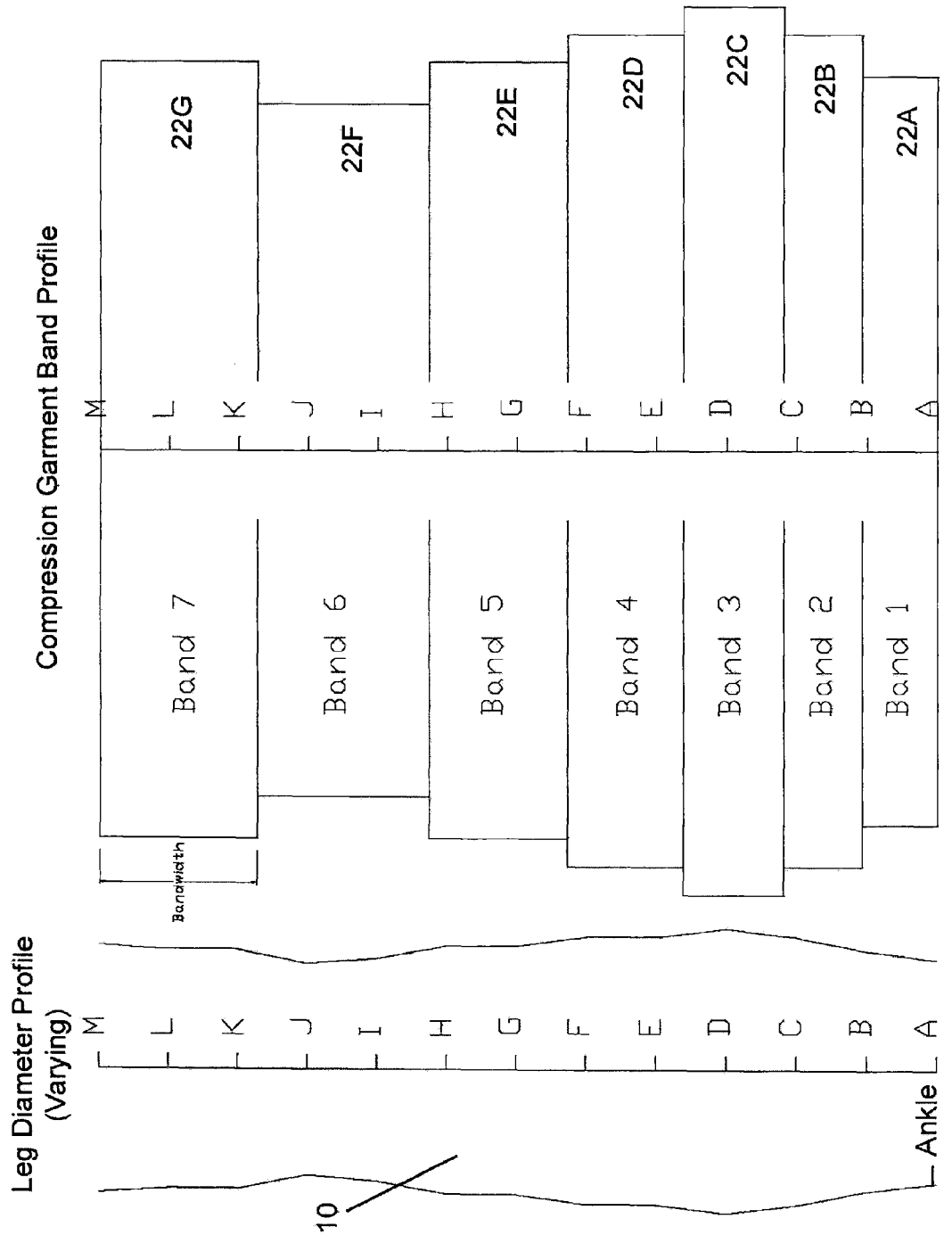

FIG. 5 is an illustration of a varying leg circumference profile, and a compression garment designed to achieve the desired compression profile. The desired compression profile is 30-40 mmHg of compression at the ankle with a compression profile that progressively decreases along the length of the leg (from location A to M—i.e.: from the groin to the ankle).

Table 3A is a leg dimension profile corresponding to FIG. 5.

Table 3B is a compression garment dimension profile and compression corresponding to FIG. 5.

DETAILED DESCRIPTION OF THE DRAWINGS

The present invention provides a method of applying therapeutic compression to a patient's body limb, comprising: (a) measuring the dimensions of a patient's body limb; (b) determining a desired compression profile for the patient's body limb; and (c) forming a compression device comprising a plurality of tension bands dimensioned to be wrapped around the patient's limb, wherein different tension bands have different widths such that applying an equal tension to the bands results in different compressions being applied along the length of the patient's limb such that the desired compression profile is applied to the patient's limb.

The manufacture and operation of the present invention is seen in the attached Figs. as follows.

Figure 1:
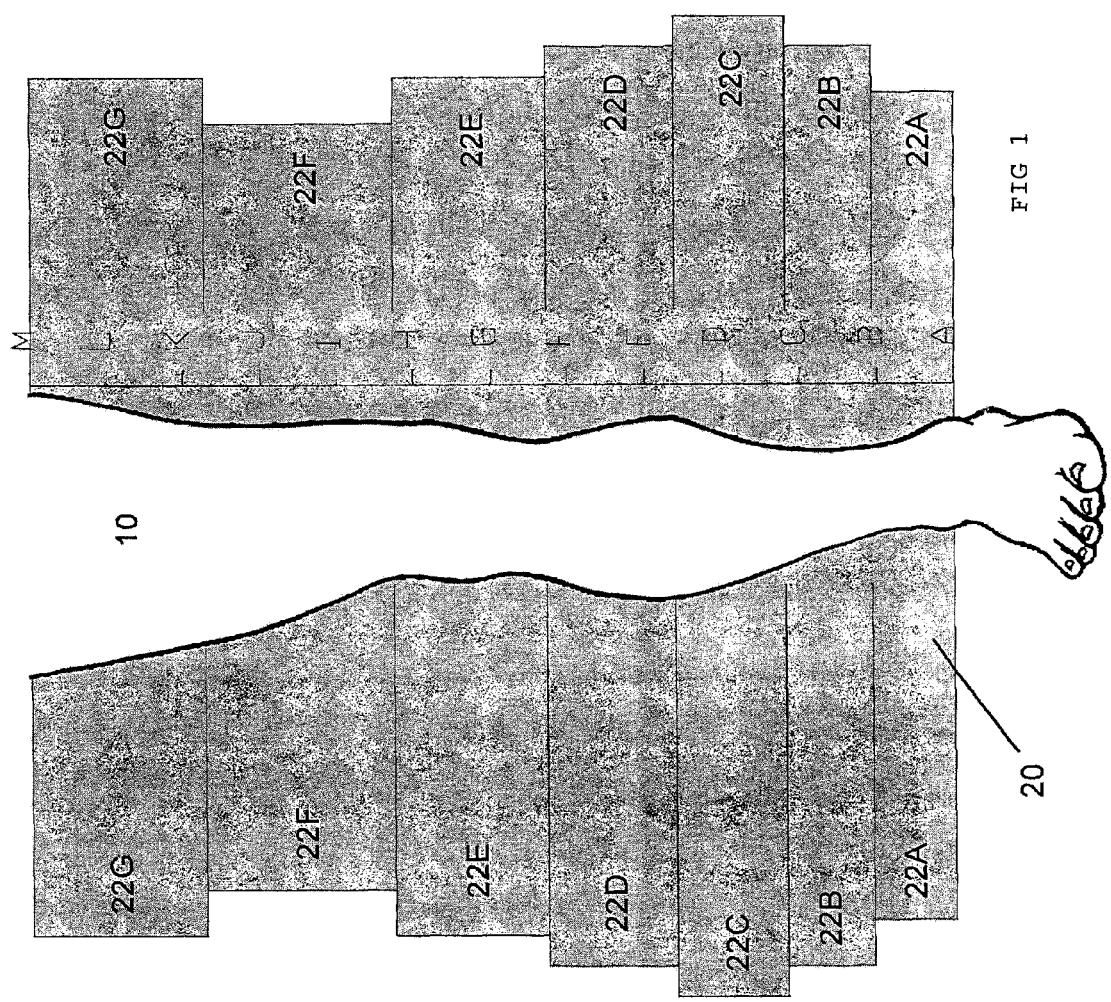
FIG. 1 is an illustration of the present compression garment prior to being applied to a patient's leg (showing 13 locations "A" to "M" along the leg).
Figure 2:
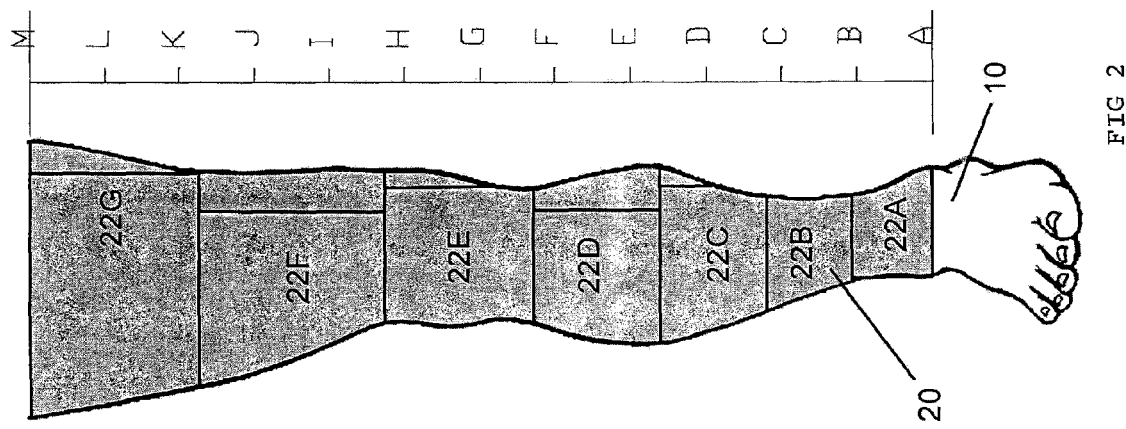
FIG. 2 is an illustration of the compression garment of FIG. 1 wrapped around the patient's leg.

FIG. 1 is an illustration of the present compression garment prior to being applied to a patient's leg (showing 13 locations "A" to "M" along the leg from the ankle to the groin.), and FIG. 2 is a corresponding illustration of the compression garment wrapped around the patient's leg.

FIGS. 3, 4 and 5 illustrate three different leg circumference profile scenarios, and the devices built to achieve a typical gradient compression profile with 30-40 mmHg of pressure at the ankle.

Turning first to FIG. 1, a patient's leg 10 is shown. (It is to be understood that the present invention can equally well be applied to a patient's arm). A compression garment/device 20 is also shown. Compression device 20 has an elongated body with a plurality of tension bands 22A, 22B, 22C, 22D, 22E, 22F and 22G. As shown in FIG. 2, device 20 is wrapped around the patient's leg 10 and then tension bands 22A, 22B, 22C, 22D, 22E, 22F and 22G are tightened to provide compression to the leg.

Systems having compression bands that are tightened around a patient's leg or arm to provide therapeutic compression (for example to treat of edema, lymphedema and various venous disorders) are found in US Patent Applications 2007/0276310 entitled "Therapeutic Sleeve For Applying Compression to A Body Part" and 2005/1092525, entitled "Limb Encircling Therapeutic Compression Device", incorporated herein by reference in their entirety for all purposes.

In contrast to these existing systems, the present invention achieves a desired compression profile that is individually tailored to a particular patient (or group of patients) needs by designing the width of tension bands 22A, 22B, 22C, 22D, 22E, 22F and 22G to preferred dimensions. FIGS. 1 and 2 illustrate an exemplary compression device having seven tension bands. It is to be understood, however, that the present invention is not limited to any particular number of tension bands, and that systems with more or less than seven tension bands 22 are also encompassed within the scope of the present invention.

Skin surface pressures underneath a bandage on a limb are best described according to La Place's law:

$$\text{Pressure (mmHg)} = \frac{\text{Tension}(Kfg) \times n \times 4620}{\text{Circumference(cm)} \times \text{Bandage width(cm)}}$$

If Tension, number of bandage layers (n,) and bandage width are held constant, pressure is inversely related to the circumference of the limb.

In accordance with the present invention, the variable of bandage width is varied (during the design of the device) while maintaining the other variables constant. Specifically, in the present adjustable non-tubular device 20 with multi-compression bands 22, gradient compression is achieved by applying all of bands 22 with same tension, but designing the bands with differing widths based on the limb's circumference profile.

Turning to FIG. 3, a patient's leg 10 is shown. Leg 10 has thirteen locations (A, B, ... M) along its length. The circumference of the leg at each of locations A to M is measured. The circumferences and diameters of each of locations A to M are shown in Table 1A.

Knowing the patient's leg dimensions at each of these locations, a desired therapeutic pressure profile of the leg may be determined. The most commonly prescribed compression profile is gradient compression, which pertains to higher compression distally with steadily decreasing compression proximally along the limb. The highest compression distally is the prescribed compression and can be determined by a therapist or physician. These levels are often prescribed in ranges such as 20-30, 30-40, or 40-50 mmHg. In this particular patient's example, it is determined to use seven tension bands (22A to 22G) having bandwidths as set forth in Table 1B. As can be seen, an increasing pressure is applied from band 22A (18.1 mmHg) to band 22G (35 mmHg) while applying the same tension (2.7 kg F) to each of bands 22A to 22G. As can also be seen in this example, each band 22A to 22G covers more than one of the locations A to M. (For example, band 22A wraps around both locations A and B, etc.) As can be seen in FIG. 3, the particular unique design of compression garment 10 (having bands 22A to 22G) results in the illustrated increasing compression profile.

Turning next to FIG. 4, another patient's leg 10 is shown. Leg 10 has thirteen locations (A, B ... M) along its length. The circumference of the leg at each of locations A to M is measured. The circumferences and diameters of each of locations A to M are shown in Table 2A.

Knowing the patient's leg dimensions at each of these locations, a desired therapeutic pressure profile of the leg may be determined. Again gradient compression is chosen as the preferred profile. In this particular patient's example, it is also determined to use seven tension bands 22 having bandwidths as set forth in Table 2B. As can be seen, an increasing pressure is applied from band 22A (19.3 mmHg) to band 22G (35 mmHg) while applying the same tension (2.7 kg F) to each of bands 22A to 22G. As can also be seen in this example, each band 22A to 22G covers more than one of the locations A to M. (For example, band 22D wraps around both locations E and F, etc.) As can be seen in FIG. 4, the particular unique design of compression garment 10 (having bands 22A to 220) results in the illustrated decreasing compression profile.

As can be seen in FIG. 4, different bands are specifically designed to have different widths. For example, band 22G is much wider than band 22A. Therefore, when bands 22A and 22G are pulled with the same tension, the wider band 22G will exert a much smaller compression on the patient's leg 10.

Lastly, FIG. 5 illustrates yet another patient's leg 10. This particular patient requires a gradient compression profile but the leg circumference profile varies (i.e.: both increases and decreases) along its length. This sort of circumference profile is the most typical where a calf has a larger circumference, which then decreases to a smaller knee area and then increases again in circumference in the thigh area. The circumference of the leg at each of locations A to M is measured. The circumferences and diameters of each of locations A to M are shown in Table 3A.

Knowing the patient's leg dimensions at each of these locations, a desired therapeutic pressure profile of the leg may be determined. Again, gradient compression is the profile chosen. In this particular patient's example, it is also determined to use seven tension bands having bandwidths as set forth in Table 3B. As can be seen, a higher pressure is applied by band 22C (21.3 mmHg) than by band 22F (16.2 mmHg). Band 22F is the widest as it has the smallest circumference profile (I and J circumference) and is more proximally located farther up the leg than compared to the similar ankle circumference (at A), which has a thinner band 22A.

An advantage of the present invention is that it can essentially be adapted to any multi-band compression garment regardless of the band design or method of tightening and adjusting each band so as long as they can be pulled to equal tensions. The present invention it is not a tubular device with compression levels preset and manufactured into the garment. Instead, it may comprise an adjustable garment with bands and not initially a tubular device. It may also optionally also comprise a mesh, foam or elastic sleeve that can be used to guide the user in putting it on or lightly hold the device onto the limb while the user tightens the bands. It can also range in design from completely elastic to completely non-elastic devices.

Thus, the present invention also provides a compression garment for applying therapeutic compression to a patient's body limb, comprising: an elongated body dimensioned to be wrapped around a length of a patient's limb to apply a therapeutic compression to the limb; and a plurality of tension bands along the length of the elongated body, the tension bands being of different widths such that applying an equal tension to the bands results in different compressions being applied by the bands along the length of the patient's limb. The elongated body and the tension bands are manufactured based upon measurements of a particular patient's body limb and a desired compression profile for the particular patient's body limb such that a desired compression profile is applied to the patient's limb when the tension bands are wrapped around the patient's limb. The user simply applies the compression garment that is pre-fabricated to their limb shape and then tightens the bands to equal tensions.

TABLE 1a

Increasing Leg Profile

| Location | Circumference (cm) | Diameter (cm) |
|---|---|---|
| A | 36 | 11.5 |
| B | 38 | 12.1 |
| C | 40 | 12.7 |
| D | 42 | 13.4 |
| E | 44 | 14.0 |

TABLE 1a-continued

Increasing Leg Profile

| Location | Circumference (cm) | Diameter (cm) |
|---|---|---|
| F | 46 | 14.6 |
| G | 48 | 15.3 |
| H | 50 | 15.9 |
| I | 52 | 16.6 |
| J | 54 | 17.2 |
| K | 56 | 17.8 |
| L | 58 | 18.5 |
| M | 60 | 19.1 |

TABLE 1b

Increasing Leg Profile

| Band # | Bandwidth (cm) | Tension (kg F) | Pressure (mmHg) |
|---|---|---|---|
| 1 | 9.5 | 2.7 | 35.0 |
| 2 | 10.5 | 2.7 | 28.6 |
| 3 | 10.5 | 2.7 | 26.6 |
| 4 | 10.5 | 2.7 | 24.9 |
| 5 | 11.5 | 2.7 | 21.0 |
| 6 | 11.5 | 2.7 | 19.5 |
| 7 | 11.5 | 2.7 | 18.1 |
| Garment Length (cm) 75.5 | | | |

TABLE 2a

Decreasing Leg Profile

| Location | Circumference (cm) | Diameter (cm) |
|---|---|---|
| A | 60 | 19.1 |
| B | 58 | 18.5 |
| C | 56 | 17.8 |
| D | 54 | 17.2 |
| E | 52 | 16.6 |
| F | 50 | 15.9 |
| G | 48 | 15.3 |
| H | 46 | 14.6 |
| I | 44 | 14.0 |
| J | 42 | 13.4 |
| K | 40 | 12.7 |
| L | 38 | 12.1 |
| M | 36 | 11.5 |

TABLE 2b

Decreasing Leg Profile

| Band # | Bandwidth (cm) | Tension (kg F) | Pressure (mmHg) |
|---|---|---|---|
| 1 | 6.0 | 2.7 | 35.0 |
| 2 | 7.5 | 2.7 | 29.0 |
| 3 | 9.0 | 2.7 | 25.5 |
| 4 | 10.5 | 2.7 | 23.1 |
| 5 | 12.0 | 2.7 | 22.0 |
| 6 | 14.0 | 2.7 | 20.6 |
| 7 | 16.5 | 2.7 | 19.3 |
| Garment Length (cm) 75.5 | | | |

TABLE 3a

Varying Leg Profile

| | Location Circumference (cm) | Diameter (cm) |
|---|---|---|
| A | 50 | 15.9 |
| B | 54 | 17.2 |
| C | 60 | 19.1 |
| D | 64 | 20.4 |
| E | 60 | 19.1 |
| F | 60 | 19.1 |
| G | 56 | 17.8 |
| H | 56 | 17.8 |
| I | 50 | 15.9 |
| J | 48 | 15.3 |
| K | 54 | 17.2 |
| L | 54 | 17.2 |
| M | 56 | 17.8 |

TABLE 3b

Varying Leg Profile

| Band # | Bandwidth (cm) | Tension (kg F) | Pressure (mmHg) |
|---|---|---|---|
| 1 | 6.8 | 2.7 | 35.0 |
| 2 | 7.0 | 2.7 | 30.8 |
| 3 | 9.0 | 2.7 | 21.3 |
| 4 | 10.5 | 2.7 | 19.5 |
| 5 | 12.5 | 2.7 | 17.6 |
| 6 | 15.5 | 2.7 | 16.2 |
| 7 | 14.2 | 2.7 | 16.0 |
| Garment Length (cm) 75.5 | | | |

What is claimed is:

1. A method of fabricating a compression device to apply therapeutic compression to a particular patient's body limb, comprising:
   (a) measuring the dimensions of the particular patient's body limb at a plurality of different lengths along the body limb;
   (b) determining a desired compression profile for the particular patient's body limb at the plurality of different lengths along the body limb; and
   (c) manufacturing a compression device comprising a plurality of tension bands dimensioned to be wrapped around the patient's limb, wherein different tension bands have different widths such that applying an equal tension to the bands results in different compressions being applied along the length of the particular patient's limb such that the desired compression profile is applied to the particular patient's limb, wherein the compression device is manufactured for the particular patient after steps (a) and (b) have been completed.

2. The method of claim 1, wherein measuring the dimensions of a patient's body limb comprises determining the circumference of the body limb at different lengths along the body limb.

3. The method of claim 1, wherein determining a desired compression profile for the patient's body limb comprises determining a graduated compression profile that increases along a portion of the patient's body limb.

4. The method of claim 1, wherein determining a desired compression profile for the patient's body limb comprises determining a graduated compression profile that decreases along a portion of the patient's body limb.

5. The method of claim 1, wherein determining a desired compression profile comprises determining a compression profile that both increases and decreases along a portion of the patient's body limb.

6. The method of claim 1, wherein manufacturing the tension bands of the compression device with increasing bandwidth along the length of the limb decreases the compression along the length of the limb.

7. The method of claim 1, wherein manufacturing the tension bands of the compression device with decreasing bandwidth along the length of the limb increases the compression along the length of the limb.

8. The method of claim 1, wherein determining a desired compression profile for the patient's body limb comprises determining desired compression levels at various distances along the length of the limb and thereby determining the widths of the bands.

9. The method of claim 1, wherein the bands are designed with different widths based upon the desired compression profile.

10. The method of claim 1, further comprising:
    (d) wrapping the tension bands of the compression device around the patient's limb; and
    (e) applying equal tension to the bands, such that the different bands apply different pressures along the length of the limb, thereby applying the desired compression profile to the patient's limb.

11. The method of claim 1, further comprising:
    (d) re-measuring the dimensions of the particular patient's body limb at a later time;
    (e) re-determining the desired compression profile for the particular patient's body limb at the later time; and
    (f) manufacturing a second compression device by varying the widths of the plurality of tension bands of the first compression device.

12. The method of claim 1, wherein the compression device is formed to the shape of the limb of the particular patient.

* * * * *